(12) United States Patent
Yu et al.

(10) Patent No.: US 6,284,902 B1
(45) Date of Patent: Sep. 4, 2001

(54) PROCESS FOR MANUFACTURING AN OPTICALLY ACTIVE (S)-3,4-EPOXYBUTYRIC ACID SALT

(75) Inventors: Ho Sung Yu; Jae Young Bae, both of Junmin-dong; Yik Haeng Cho; Young Mi Park, both of Songkang-dong; Il Suk Byun, Doonsan-1 dong, all of (JP)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 0 days.

(21) Appl. No.: 09/744,296

(22) PCT Filed: Dec. 8, 1998

(86) PCT No.: PCT/KR98/00410

§ 371 Date: Feb. 21, 2001

§ 102(e) Date: Feb. 21, 2001

(87) PCT Pub. No.: WO00/05227

PCT Pub. Date: Feb. 3, 2000

(30) Foreign Application Priority Data

Jul. 24, 1998 (KR) .................................................. 98-29911

(51) Int. Cl.$^7$ ....................... C07D 301/26; C07D 301/28
(52) U.S. Cl. ........................................... 549/520; 549/557
(58) Field of Search ..................................... 549/520, 557

(56) References Cited

FOREIGN PATENT DOCUMENTS 0 237 983 A2    9/1987   (EP) .

Primary Examiner—Ba K. Trinh
(74) Attorney, Agent, or Firm—Lowe Hauptman Gilman & Berner, LLP

(57) ABSTRACT

This invention relates to a process for manufacturing an optically active (S)-3,4-epoxybutyric acid salt and more particularly, to a method for manufacturing (S)-3,4-epoxybutyric acid salt expressed by the following formula 1, wherein an optically active (S)-3-hydroxybutyrolactone is employed to undergo an economical ring-opening reaction and epoxydation so that its chiral center is maintained in an original form, Formula 1

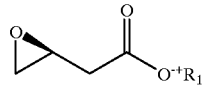

Wherein, $R_1$ represents alkali metal atom, alkaline earth metal atom, alkylamine group or quarternary amine group.

5 Claims, No Drawings

PROCESS FOR MANUFACTURING AN OPTICALLY ACTIVE (S)-3,4-EPOXYBUTYRIC ACID SALT

This application is a 371 of PCT/KR 98/00410 filed Dec. 8, 1998.

BACKGROUND OF THE INVENTION

1. Field of the Invention

This invention relates to a process for manufacturing an optically active (S)-3,4-epoxybutyric acid salt and more particularly, to a method for manufacturing (S)-3,4-epoxybutyric acid salt expressed by the following formula 1, wherein an optically active (S)-3-hydroxybutyrolactone is employed to undergo an economical ring-opening reaction and epoxydation so that its chiral center is maintained in an original form.

Formula 1

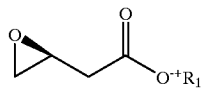

Wherein, $R_1$ represents alkali metal atom, alkaline earth metal atom, alkylamin group or quarternary amine group.

2. Description of the Related Art

An (S)-3,4-epoxybutyric acid salt expressed by the above formula 1 is a pivotal compound as an indispensable intermediate of various chiral drugs because of the synethetic usefulness of epoxy group. In particular, since (S)-3,4-epoxybutyric acid salt expressed by the above formula 1 has a better reactivity under aqueous solution, its availability in various chemical reaction has a broader scope in related fields.

The optically active (S)-3,4-epoxybutyric acid salt has the industrial application as raw material of drugs which may be contained in the cerebral enhancers and senile dementia drugs, antibiotics, antihypertensives and antihyperlipidemia.

The typical manufacturing methods related to (S)-3,4-epoxybutyric acid salt developed hitherto and some compounds with similar reactivity are as follows:

A method of manufacturing (S)-3,4-epoxybutyric acid salt was to introduce epoxy group sterically via asymmetric epoxydation and oxidation in a sequence but the extremely low yield and optical purity of the desired compound (yield: 11~25%, optical purity: 55%) proven to be inadequate for industrial use [J. Org. Chem., 49,3707(1984)].

According to another method [(Helv. Chim. Acta, 70, 142(1987) and European Pat. No. 237,983], it disclosed a method of manufacturing (S)-3,4-epoxybutyric acid salt, wherein a racemic 3,4-epoxybutyric acid ester was prepared and followed by the use of an enzyme based on an optical separation method. This method was proven to have been effective in optical purity but more than 50% yield could not be obtained in consideration of prolonged reaction time, maintenance of reaction conditions in enzyme and optical separation reaction in the light of biological reaction.

In addition, a method of manufacturing (S)-3,4-epoxybutyric acid ester from (S)-3-hydroxybutyrolactone was disclosed (Tetrahedron Letters 28, 1781(1987); Tetrahedron 46, 4277 (1990) and International Patent Publication No. WO93/06826). Its manufacturing process is described in the following scheme 1.

Scheme 1

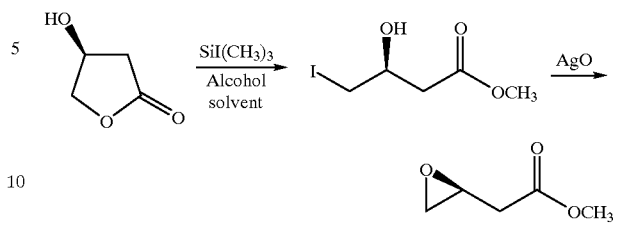

The scheme 1 has recognized some disadvantages in that a) with a high-priced iodotrimethyl silane ($SiI(CH_3)_3$) reagent for iodination and esterification, the reaction should be performed in the presence of anhydrous solvent, b) during epoxydation, a high-priced silver oxide (AgO) reagent should be uneconomically employed, and c) since (S)-3,4-epoxybutyric acid ester, so prepared from the conventional methods has no reactivity in an aqueous solution, its scope of use is extremely restricted. For example, a glycine derivative is insoluble to organic solvents, so it should be modified with benzylaldehye first so as to enhance its solubility to organic solvent during the amination between (S)-3,4-epoxybutyric acid ester and glycine derivative. 4-Hydroxy-2-butenic acid ester is also generated as a byproduct due to elimination reaction associated with the basicity of glycine derivative, when it reacts with (S)-3,4-epoxybutyric acid ester.

By contrast, (S)-3,4-epoxybutyric acid salt, a final product of this invention having a better reactivity in an aqueous solution may be directly aminated with glycine or glycine derivative in an aqueous solution, thus simplifying the complicated manufacturing process.

SUMMERY OF THE INVENTION

As a result of intensive studied performed by the inventor et al. in an effort to develop a process for manufacturing an industrially useful (S)-3,4-epoxybutyric acid salt having an excellent reactivity in an aqueous solution in an effective manner, this invention designed to manufacture the desired compound has been finally completed in such a manner that (S)-3-hydroxybutyrolactone is used as a starting material which may be synthesized from the inexpensive and easily obtainable lactose, followed by a ring-opening reaction using halogen acid-carboxylic acid and epoxydation in the presence of base.

Therefore, an object of this invention is to provide a process for manufacturing a high-purity (S)-3,4-epoxybutyric acid salt with high yield using low-priced reagents without any high-priced reagents or with handling difficulty, as in the conventional method.

Further, the process for manufacturing (S)-3,4-epoxybutyric acid salt according to this invention, which has not been applicable in the related field hitherto, is an economical technology designed to manufacture (S)-3,4-epoxybutyric acid salt in high optical purity via the conversion of an optically active (S)-3-hydroxybutyrolactone, a starting material, to a butyric acid derivative. Thus, this invention is a pioneer in terms of its novelty and application.

DETAILED DESCRIPTION OF THE INVENTION

This invention is characterized by a process for manufacturing (S)-3,4-epoxybutyric acid salt expressed by the following formula 1, wherein the ring-opening reaction of (S)-3-hydroxybutyrolactone expressed by the following formula 2 is performed using halogen acid-carboxylic acid to give a butyric derivative expressed by the following formula 3 and then said derivative is epoxidated in the presence of a base and aqueous solution at the temperature range of −20° C.~100° C.

Formula 1

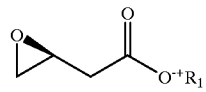

Formula 2

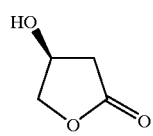

Formula 3

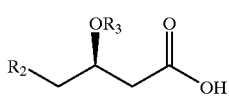

Where, $R_1$ is determined depending on the kinds of base used and represents alkali metal atom, alkaline earth metal atom, alkylamine group or quarternary amine group; $R_2$ represents halogen group which may enable the epoxidation; $R_3$ represents hydrogen atom or acyl group.

The following scheme 2 is a schematic diagram illustrating the manufacturing process of (S)-3,4-epoxybutyric acid salt according to this invention:

Scheme 2

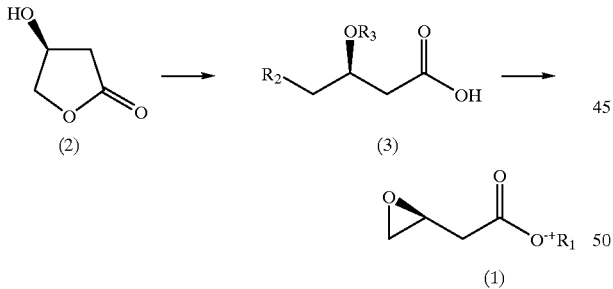

From the above scheme, $R_1$, $R_2$ and $R_3$ are the same as defined above, respectively.

(S)-3-hydroxybutyrolactone expressed by the formula 2, a starting material of this invention, is synthesized from lactose based on the method as disclosed in European Patent No.513,430.

The ring-opening reaction of (S)-3-hydroxybutyrolactone expressed by the formula 2 is performed in the presence of carboxylic acid containing halogen acid at the constant temperature of 0~150° C. The ring-opening reaction is generally performed in the presence of halogen acid and alcohol solvent. But after the reaction is completed, an epoxide ester compound whose chemical reaction may be available in organic solvent only may be obtained. It is not in the form of epoxide salt which may be reacted in an aqueous solution. The epoxide ester compound is not easily reacted with nucleophilic materials which is insoluble to organic solvents, and 4-hydroxy-2-butenic acid ester as a byproduct is generated due to elimination reaction caused by the basicity of nucleophilic materials.

By contrast, this invention is characterized in that an optically-active (S)-epoxide salt as a final product may be obtained in such a manner to use a mixture of halogen acid and carboxylic acid and to react a base in an aqueous solution. In an aqueous solution, the final product may be easily reacted with nucleophilic materials which is insoluble to organic solvents and without elimination reaction, chiral intermediates for various drugs may be easily synthesized. In addition, the final product of this invention is an useful intermediate which may react with any nucleophilic materials in the presence of organic solvents in that it may acidify an optically active (S)-epoxide salt to form (S)-epoxide acid and then such acid is reacted with an alcohol solvent under a mild acid condition to yield (S)-epoxide ester.

The example of carboxylic acid used from the ring-opening reaction include alkylcarboxylic acid having carbon atoms of 1~4 including acetic acid, while that of halogen acid includes hydrochloric acid and hydrobromic acid.

It is preferred that the amount of halogen acid and carboxylic acid is in the volumetric ratio of 1:1~1:3; if an excess of carboxylic acid is used, the reaction rate is slow and the removal of carboxylic acid in excess is not easily made available. In addition, when an excess of halogen acid is used, larger amount of base is inevitably added from the next reaction process whereby the accurate amount of base should be predetermined so as not to prevent any side reaction associated with base. It is preferred that the ring-opening reaction temperature is maintained at 0~150° C.

Through the aforementioned ring-opening reaction, (S)-butyric acid derivative expressed by the formula 3 may be synthesized without any loss of optical activity in the absence of any byproducts.

As a final step, the (S)-butyric derivative expressed by formula 3 is reacted with a base to yield (S)-3,4-epoxybutyric acid salt expressed by the formula 1, while maintaining the chirality.

Such epoxydation mechanism may be expressed by the following scheme 3.

Scheme 3

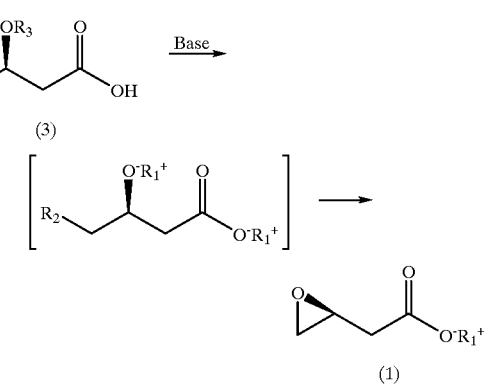

Where, $R_1$, $R_2$ and $R_3$ are the same as defined above, respectively.

Examples of a base from the epoxydation include alkali metal hydroxide such as sodium hydroxide, potassium hydroxide and lithium hydroxide; alkaline earth metal hydroxide such as magnesium hydroxide, calcium hydroxide and barium hydroxide; alkali metal alkoxide such as sodium methoxide, sodium ethoxide, potassium t-buthoxide; alkylamine expressed by $NHR_4R_5$ (hence, $R_4$ and $R_5$, respectively, is an alkyl group having carbon atoms of 2~7) and $NH_2R_6$ ($R_6$ is an alkyl group having carbon atoms of 3~9); quarternary hydroxide such as tetrabutylammonium hydroxide and benzyltrimethylammonium hydroxide.

The epoxydation is performed in the presence of base at −20~100° C.; hence, the reaction solvent includes water as a single solvent or a co-solvent containing organic solvent with water, if deemed necessary. If a co-solvent is employed, a small amount of organic solvent is added to water and examples of organic solvent with water include alcohol with carbon atoms of 1~4, tetrahydrofuran, dioxane and acetonitrile.

The following specific examples are intended to be illustrative of the invention and should not be construed as limiting the scope of the invention as defined by appended claims.

EXAMPLE 1
Preparation of (S)-3-acetoxy-4- bromobutyric acid

A solution of (S)-3-hydroxybutyrolactone (10 g) in 85% purity and hydrogen bromide/acetic acid (40 ml) in 30% purity was charged to a 250 ml flask equipped with a thermometer, reflux condensor and agitator, and stirred at 40~60° C. for 5 hours. After the reaction was completed, the reaction solution was cooled at room temperature. With the addition of methylene chloride (200 ml), the mixture washed with 1M sodium acetate solution and then an organic layer was separated, dried over anhydrous magnesium sulfate, filtered off and concentrated. Toluene (100 ml) was added to (S)-3-acetoxy-4-bromobutyric acid, so concentrated, to remove the remaining acetic acid. The concentration under reduced pressure gave 18.74 g of (S)-3-acetoxy-4-bromobutyric acid (yield: 85%).

$^1$H-NMR(CDCl$_3$,ppm): δ2.1(s, 3H, CH$_3$COO), 2.8~2.9 (dd, 2H, CH$_2$COOH), 3.5~3.6(dd, 2H, BrCH$_2$CH), 5.3~5.4 (m, 1H, CHCOCOCH$_3$).

EXAMPLE 2
Preparation of(S)-3,4-epoxybutyric acid (S)-3-acetoxy-4-bromobutyric acid (27 g, 0.12 mol) was charged to a 1 l flask equipped with a thermometer, pH meter and agitator, and with the addition of 1N NaOH solution (363 ml, 0.363 mol) for 20 minutes dropwise, was stirred at 0~5° C. for 2 hours to give (S)-3,4-epoxybutyric acid sodium salt. The reaction solution was acidified in 1N HCl solution by adjusting its pH at 3~4, extracted by ethyl ether and dried over anhydrous magnesium sulfate. The residue was filtered off and evaporated under reduced pressure to obtain 7.8 g of (S)-3,4-epoxybutyric acid (yield: 65%).

$^1$H-NMR(D$_2$O, ppm): δ2.3~2.8(m, 2H, CH$^2$COOH), 2.6~2.9(m, 2H, 4-H), 3.3 ~3.4(m, 1H, 3-H)

$^{13}$C-NMR(D$_2$O, ppm): δ37.56(CH$_2$COOH), 49.47(4-CH$_2$), 47.75(3-CH), 175.43(COOH)

EXAMPLE 3
Preparation of (S)-3,4-epoxybutyric acid sodium salt (S)-3-acetoxy-4-bromobutyric acid (0.9 g, 0.004 mol) was charged to 100 ml flask equipped with a thermometer, pH meter and agitator, and with the addition of 1N NaOH solution (12 ml, 0.012 mol) for 20 minutes dropwise, and stirred at 0~5° C. for 2 hours to give (S)-3,4-epoxybutyric acid sodium salt. It was confirmed by a Nuclear Magnetic Resonance (NMR) analysis that more than 99% (S)-3,4-epoxybutyric acid sodium was converted.

$^1$H-NMR(D$_2$O, ppm): δ2.3~2.5(m, 2H, CH$_2$COONa), 2.6~2.9(m, 2H, 4-H), 3.2~3.3(m, 1H, 3-H)

$^{13}$C-NMR(D$_2$O, ppm): δ40.87(CH$_2$COONa), 48.24(4-CH$_2$), 51.08(3-CH), 179.41(COONa)

EXAMPLE 4
Preparation of (S)-3,4-epoxybutyric acid sodium salt

A solution of distilled water (10 ml), (S)-3-acetoxy-4-bromobutyric acid (0.9 g, 0.004 mol) and sodium methoxide (0.654 g, 0.012 mol) was charged to 100 ml flask equipped with a thermometer, pH meter and agitator, and stirred at 0~5° C. for 2 hours to give (S)-3,4-epoxybutyric acid sodium salt. It was confirmed by a NMR analysis that more than 99% (S)-3,4-epoxybutyric acid sodium salt was converted.

$^1$H-NMR(D$_2$O, ppm): δ2.3~2.5(m, 2H, CH$_2$COONa), 2.6~2.9(m, 2H, 4-H), 3.2~3.3(m, 1H, 3-H)

EXAMPLE 5
Preparation of (S)-3,4-epoxybutyric acid calcium salt

A solution of distilled water (10 ml), (S)-3-acetoxy-4-bromobutyric acid (0.9 g, 0.004 mol) and calcium hydroxide (0.45 g, 0.006 mol) was charged to 100 ml flask equipped with a thermometer, pH meter and agitator, and stirred at 0~5° C. for 2 hours to give (S)-3,4-epoxybutyric acid calcium salt. It was confirmed by a NMR analysis that more than 99% (S)-3,4-epoxybutyric acid calcium salt was converted.

$^1$H-NMR(D$_2$O, ppm): δ2.3~2.4(m, 2H, CH$_2$COOCa), 2.5~2.8(m, 2H, 4-H), 3.2~3.3(m, 1H, 3-H)

EXAMPLE 6
Preparation of (S)-3,4-epoxybutyric acid tetrabutylammonium salt

A solution of distilled water (10 ml), (S)-3-acetoxy-4-bromobutyric acid (0.9 g, 0.004 mol) and 1.0M methanol (12 ml, 0.012 mol) in tetrabutylammonium hydroxide was charged to 100 ml flask equipped with a thermometer, pH meter and agitator, and stirred at 0~5° C. for 2 hours to give (S)-3,4-epoxybutyric acid tetrabutylammonium salt. It was confirmed by a NMR analysis that more than 99% (S)-3,4-epoxybutyric acid tetrabutylammonium salt was converted.

$^1$H-NMR(D$_2$O, ppm): δ2.2~2.3(m, 2H, CH$_2$COONBu$_4$), 2.5~2.8(m, 2H, 4-H), 3.2~3.3(m, 1H, 3-H)

EXAMPLE 7
Preparation of (S)-3,4-epoxybutyric acid triethylamine salt

A solution of distilled water (10 ml), (S)-3-acetoxy-4-bromobutyric acid (0.9 g, 0.004 mol) and triethylamine (1.21 g, 0.012 mol) was charged to 100 ml flask equipped with a thermometer, pH meter and agitator, and stirred at 0~5° C. for 2 hours to give (S)-3,4-epoxybutyric acid triethylamine salt. It was confirmed by a NMR analysis that more than 99% (S)-3,4-epoxybutyric acid triethylamine salt was converted.

$^1$H-NMR(D$_2$O, ppm): δ2.2~2.4(m, 2H, CH2COONEt$_3$), 2.5~2.8(m, 2H, 4-H), 3.1~3.2(m, 1H, 3-H)

EXAMPLE 8
Preparation of (S)-3,4-epoxybutyric acid diisopropylamine salt

A solution of distilled water (10 ml), (S)-3-acetoxy-4-bromobutyric acid (0.9 g, 0.004 mol) and diisopropylamine (1.21 g, 0.012 mol) was charged to 100 ml flask equipped with a thermometer, pH meter and agitator, and stirred at 0~5° C. for 2 hours to give (S)-3,4-epoxybutyric acid diisopropylamine salt. It was confirmed by a NMR analysis that more than 99% (S)-3,4-epoxybutyric acid diisopropylamine salt was converted.

$^1$H-NMR(D$_2$O, ppm): δ2.2~2.4(m, 2H, CH$_2$COONH$_2$iPr$_2$), 2.5~2.8(m, 2H, 4-H), 3.1~3.2(m, 1H, 3-H)

EXAMPLE 9

Preparation of (S)-3,4-epoxybutyric acid t-butylamine salt

A solution of distilled water (10 ml), (S)-3-acetoxy-4-bromobutyric acid (0.9 g, 0.004 mol) and t-butylamine (0.08 g, 0.012 mol) was charged to 100 ml flask equipped with a thermometer, pH meter and agitator, and stirred at 0~5° C. for 2 hours to give (S)-3,4-epoxybutyric acid t-butylamine salt. It was confirmed by a NMR analysis that more than 99% (S)-3,4-epoxybutyric acid t-butylamine salt was converted.

$^1$H-NMR(D$_2$O, ppm): δ2.1~2.4(m, 2H, CH$_2$COONH$_3$But), 2.5~2.8(m,2H,4-H), 3.1~3.2(m, 1H, 3-H)

As described above, this invention has several advantages in that a) (S)-3,4-epoxybutyric acid salt in high purity may be prepared with high yield using an inexpensive reagent for reaction, b) since (S)-3,4-epoxybutyric acid salt, so prepared according to this invention, may be easily reacted with various nuclophilic chemical compounds in aqueous solution, a variety of nucleophiles containing oxygen, nitrogen, acid, sulfur and carbon nucleophile and epoxide salt, being insoluble to organic solvents, are subject to ring-opening reaction so that various industrially useful chiral derivatives can be manufactured.

What is claimed is:

1. A process for manufacturing (S)-3,4-epoxybutyric acid salt expressed by the following formula 1, wherein the ring-openning reaction of (S)-3-hydroxybutyrolactone expressed by the following formula 2 is performed using halogen acid-carboxylic acid to give a butyric derivative expressed by the following formula 3 and then said derivative is epoxidated in the presence of a base and aqueous solution at the temperature range of −20° C.~100° C.

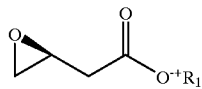

Formula 1

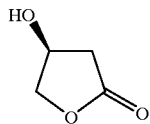

Formula 2

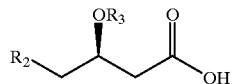

Formula 3

Where, R$_1$ represents alkali metal atom, alkaline earth metal atom, alkylamine group or quarternary amine group; R$_2$ represents halogen group; R$_3$ represents hydrogen atom or aliphatic acyl group.

2. The process for manufacturing (S)-3,4-epoxybutyric acid salt according to 1, wherein said epoxydation is performed in the presence of water as a single solvent or of co-solvent containing a small amount of organic solvent with water, if deemed necessary.

3. The process for manufacturing (S)-3,4-epoxybutyric acid salt according to 2, wherein said organic solvent used with water is selected from the group consisting of alcohol with carbon atoms of 1~4, tetrahydrofuran, dioxane and acetonitrile.

4. The process for manufacturing (S)-3,4-epoxybutyric acid salt according to 1, wherein a base used for said epoxydation is selected from the group consisting of alkali metal hydroxide, alkaline earth metal hydroxide, alkali metal alkoxide, alkylamine and quarternary amine hydroxide.

5. The process for manufacturing (S)-3,4-epoxybutyric acid salt according to 4, wherein said alkali metal hydroxide is selected from the group consisting of sodium hydroxide, sodium potassium and lithium hydroxide; said alkaline earth metal hydroxide is selected from the group consisting of magnesium hydroxide, calcium hydroxide and barium hydroxide; said alkali metal alkoxide is selected from the group consisting of sodium methoxide, sodium ethoxide and potassium t-buthoxide; said alkylamine is selected from the group consisting of NHR$_4$R$_5$ (hence, R$_4$ and R$_5$, respectively, is an alkyl group having carbon atoms of 2~7) and NH$_2$R$_6$ (R$_6$ is an alkyl group having carbon atoms of 3~9); said quarternary amine hydroxide is selected from the group consisting of tetrabutylammonium hydroxide and benzyltrimethylammonium hydroxide.

* * * * *

UNITED STATES PATENT AND TRADEMARK OFFICE
CERTIFICATE OF CORRECTION

PATENT NO.     : 6,284,902 B1                                Page 1 of 1
DATED          : September 4, 2001
INVENTOR(S)    : Ho Sung Yu et al.

It is certified that error appears in the above-identified patent and that said Letters Patent is hereby corrected as shown below:

Title page,
Item, [75] Inventors:    Ho Sung Yu; Jae Young Bae, both of Junmin-dong; Yik Haeng Cho; Young Mi Park, both of Songkang-dong; Il Suk Byun, Doonsan-1 dong, all of (KR)

Signed and Sealed this

Twenty-eighth Day of May, 2002

Attest:

JAMES E. ROGAN
Attesting Officer        *Director of the United States Patent and Trademark Office*